United States Patent
Patel et al.

(10) Patent No.: US 9,670,125 B2
(45) Date of Patent: Jun. 6, 2017

(54) METHODS OF MAKNG HIGH-PURITY DIBASIC ACID COMPOSITIONS

(71) Applicant: Elevance Renewable Sciences, Inc., Woodridge, IL (US)

(72) Inventors: Alpeshkumar K. Patel, Woodridge, IL (US); Yenamandra Viswanath, Woodridge, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/673,509

(22) Filed: Mar. 30, 2015

(65) Prior Publication Data

US 2015/0274630 A1   Oct. 1, 2015

Related U.S. Application Data

(63) Continuation-in-part of application No. 14/502,382, filed on Sep. 30, 2014.

(60) Provisional application No. 61/888,440, filed on Oct. 8, 2013.

(51) Int. Cl.
| | |
|---|---|
| *C07C 51/48* | (2006.01) |
| *C07C 51/09* | (2006.01) |
| *C07C 51/43* | (2006.01) |

(52) U.S. Cl.
CPC .............. *C07C 51/48* (2013.01); *C07C 51/09* (2013.01); *C07C 51/43* (2013.01)

(58) Field of Classification Search
CPC .......... C07C 51/48; C07C 51/09; C07C 51/43
USPC ....................................................... 562/590
See application file for complete search history.

(56) References Cited

U.S. PATENT DOCUMENTS

| | | |
|---|---|---|
| 2009/0264672 A1 | 10/2009 | Abraham et al. |
| 2013/0085288 A1 | 4/2013 | Snead et al. |
| 2013/0204022 A1 | 8/2013 | Snead et al. |
| 2014/0121402 A1 | 5/2014 | Snead et al. |
| 2015/0119602 A1 | 4/2015 | Patel et al. |

FOREIGN PATENT DOCUMENTS

GB   2001312   1/1979

OTHER PUBLICATIONS

Oniciu et al J. Med. Chem., 2006, 49, 334-348.*
Stempfle et al Macromolecules, 2011, 44, 4159-4166.*
Int'l Search Report and Written Opinion for PCT App. No. PCT/US2014/058359, dated Mar. 17, 2015.
Int'l Preliminary Report on Patentability for PCT App. No. PCT/US2014/058359, dated Apr. 12, 2016.

* cited by examiner

*Primary Examiner* — Yevegeny Valenrod
(74) *Attorney, Agent, or Firm* — Kilpatrick Townsend & Stockton LLP

(57) ABSTRACT

High-purity dibasic acid compositions are generally disclosed. In some embodiments, the dibasic acid compositions are solutions or suspensions. In some other embodiments, the compositions are solid-state compositions. In some such embodiments, the solid-state compositions comprise a dibasic acid as a crystalline solid and further comprise a low quantity of certain impurities, such as monobasic acids, various esters, and the like. Methods and systems for making such high-purity dibasic acid compositions are also disclosed.

11 Claims, 3 Drawing Sheets

METHODS OF MAKNG HIGH-PURITY DIBASIC ACID COMPOSITIONS

CROSS-REFERENCE TO RELATED APPLICATIONS

The present application is a continuation-in-part of U.S. patent application Ser. No. 14/502,382, filed Sep. 30, 2014, which claims the benefit of priority of U.S. Provisional Application No. 61/888,440, filed Oct. 8, 2013, both of which are hereby incorporated by reference in their entirety as though fully set forth herein.

TECHNICAL FIELD

Methods of making high-purity dibasic acid compositions are generally disclosed. In some embodiments, the methods include saponifying a dibasic ester to form a dicarboxylate compound. In some further embodiments, the methods further include acidifying the dicarboxylate compound to form a dibasic acid.

BACKGROUND

Dibasic acids are organic compounds having two carboxylic acid groups. Such compounds can be used in a wide array of different ways. Because of their difunctionality, they are commonly used in making certain polymers. For example, a polyamide can be made by reacting a dibasic acid with a diamine, i.e., an organic compound having two amine groups. As another example, a polyester can be made by reacting a dibasic acid with a diol, i.e., an organic compound having two hydroxyl groups.

In certain instances, it may be desirable to use dibasic acids in a highly pure form, as the presence of impurities may cause certain undesirable events to occur. For example, if a dibasic acid composition contains a substantial amount of monobasic acid impurity, it can cause early chain termination in the polymerization process, thereby resulting in polymer chains that may have a lower molecular weight than desired.

Thus, there is a continuing need to develop cost-effective and scalable methods of making dibasic acids that result in high-purity compositions, especially compositions that have a low concentration of monobasic acid impurity.

SUMMARY

In a first aspect, the disclosure provides methods for saponifying a dibasic ester, including: introducing a dibasic ester to a reactor; and reacting the dibasic ester in the reactor to form a dicarboxylate compound. In some embodiments, the method comprises acidifying the dicarboxylate compound to form a dibasic acid.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative, and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1:
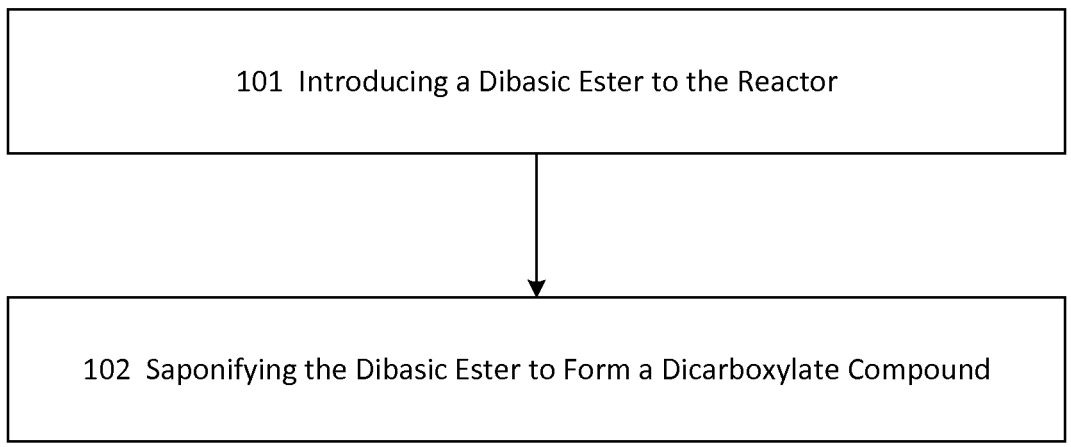
FIG. 1 shows an illustrative embodiment of a method for saponifying a dibasic ester to form a dicarboxylate compound.

The following description recites various aspects and embodiments of the inventions disclosed herein. No particular embodiment is intended to define the scope of the invention. Rather, the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

DEFINITIONS

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "natural oil," "natural feedstock," or "natural oil feedstock" refer to oils derived from plants or animal sources. These terms include natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

As used herein, "natural oil derivatives" refers to the compounds or mixtures of compounds derived from a natural oil using any one or combination of methods known in the art. Such methods include but are not limited to saponification, fat splitting, transesterification, esterification, hydrogenation (partial, selective, or full), isomerization, oxidation, and reduction. Representative non-limiting examples of natural oil derivatives include gums, phospholipids, soapstock, acidulated soapstock, distillate or distillate sludge, fatty acids and fatty acid alkyl ester (e.g. non-limiting examples such as 2-ethylhexyl ester), hydroxy substituted variations thereof of the natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil). Soybean oil typically comprises about 95% weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12-octadecadienoic acid), and linolenic acid (9,12,15-octadecatrienoic acid).

As used herein, "metathesis catalyst" includes any catalyst or catalyst system that catalyzes an olefin metathesis reaction.

As used herein, "metathesize" or "metathesizing" refer to the reacting of a feedstock in the presence of a metathesis catalyst to form a "metathesized product" comprising new olefinic compounds, i.e., "metathesized" compounds. Metathesizing is not limited to any particular type of olefin metathesis, and may refer to cross-metathesis (i.e., co-metathesis), self-metathesis, ring-opening metathesis, ring-opening metathesis polymerizations ("ROMP"), ring-closing metathesis ("RCM"), and acyclic diene metathesis ("ADMET"). In some embodiments, metathesizing refers to reacting two triglycerides present in a natural feedstock (self-metathesis) in the presence of a metathesis catalyst, wherein each triglyceride has an unsaturated carbon-carbon double bond, thereby forming a new mixture of olefins and esters which may include a triglyceride dimer. Such triglyceride dimers may have more than one olefinic bond, thus higher oligomers also may form. Additionally, in some other embodiments, metathesizing may refer to reacting an olefin, such as ethylene, and a triglyceride in a natural feedstock having at least one unsaturated carbon-carbon double bond, thereby forming new olefinic molecules as well as new ester molecules (cross-metathesis).

As used herein, "hydrocarbon" refers to an organic group composed of carbon and hydrogen, which can be saturated or unsaturated, and can include aromatic groups. The term "hydrocarbyl" refers to a monovalent or polyvalent hydrocarbon moiety.

As used herein, "olefin" or "olefins" refer to compounds having at least one unsaturated carbon-carbon double bond. In certain embodiments, the term "olefins" refers to a group of unsaturated carbon-carbon double bond compounds with different carbon lengths. Unless noted otherwise, the terms "olefin" or "olefins" encompasses "polyunsaturated olefins" or "poly-olefins," which have more than one carbon-carbon double bond. As used herein, the term "monounsaturated olefins" or "mono-olefins" refers to compounds having only one carbon-carbon double bond. A compound having a terminal carbon-carbon double bond can be referred to as a "terminal olefin," while an olefin having a non-terminal carbon-carbon double bond can be referred to as an "internal olefin."

As used herein, the term "low-molecular-weight olefin" may refer to any one or combination of unsaturated straight, branched, or cyclic hydrocarbons in the $C_{2-14}$ range. Low-molecular-weight olefins include "alpha-olefins" or "terminal olefins," wherein the unsaturated carbon-carbon bond is present at one end of the compound. Low-molecular-weight olefins may also include dienes or trienes. Low-molecular-weight olefins may also include internal olefins or "low-molecular-weight internal olefins." In certain embodiments, the low-molecular-weight internal olefin is in the $C_{4-14}$ range. Examples of low-molecular-weight olefins in the $C_{2-6}$ range include, but are not limited to: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. Non-limiting examples of low-molecular-weight olefins in the $C_{7-9}$ range include 1,4-heptadiene, 1-heptene, 3,6-nonadiene, 3-nonene, 1,4,7-octatriene. Other possible low-molecular-weight olefins include styrene and vinyl cyclohexane. In certain embodiments, it is preferable to use a mixture of olefins, the mixture comprising linear and branched low-molecular-weight olefins in the $C_{4-10}$ range. In one embodiment, it may be preferable to use a mixture of linear and branched $C_4$ olefins (i.e., combinations of: 1-butene, 2-butene, and/or isobutene). In other embodiments, a higher range of $C_{11-C14}$ may be used.

In some instances, the olefin can be an "alkene," which refers to a straight- or branched-chain non-aromatic hydrocarbon having 2 to 30 carbon atoms and one or more carbon-carbon double bonds, which may be optionally substituted, as herein further described, with multiple degrees of substitution being allowed. A "monounsaturated alkene" refers to an alkene having one carbon-carbon double bond, while a "polyunsaturated alkene" refers to an alkene having two or more carbon-carbon double bonds. A "lower alkene," as used herein, refers to an alkene having from 2 to 10 carbon atoms.

As used herein, "alpha-olefin" refers to an olefin (as defined above) that has a terminal carbon-carbon double bond. In some embodiments, the alpha-olefin is a terminal alkene, which is an alkene (as defined above) having a terminal carbon-carbon double bond. Additional carbon-carbon double bonds can be present.

As used herein, "ester" or "esters" refer to compounds having the general formula: R—COO—R', wherein R and R' denote any organic group (such as alkyl, aryl, or silyl groups) including those bearing heteroatom-containing substituent groups. In certain embodiments, R and R' denote alkyl, alkenyl, aryl, or alcohol groups. In certain embodiments, the term "esters" may refer to a group of compounds with the general formula described above, wherein the compounds have different carbon lengths. In certain embodiments, the esters may be esters of glycerol, which is a trihydric alcohol. The term "glyceride" can refer to esters where one, two, or three of the —OH groups of the glycerol have been esterified. Thus, the term "unsaturated glyceride" can refer to monoglycerides, diglycerides, or triglycerides, where one or more of the acid portions of the ester contain unsaturation, e.g., a carbon-carbon double bond.

It is noted that an olefin may also comprise an ester, and an ester may also comprise an olefin, if the R or R' group in the general formula R—COO—R' contains an unsaturated carbon-carbon double bond. Such compounds can be referred to as "olefin esters." Further, a "terminal olefin ester" may refer to an ester compound where R has an olefin positioned at the end of the chain. An "internal olefin ester" may refer to an ester compound where R has an olefin positioned at an internal location on the chain. Additionally, the term "terminal olefin" may refer to an ester or an acid thereof where R' denotes hydrogen or any organic compound (such as an alkyl, aryl, or silyl group) and R has an olefin positioned at the end of the chain, and the term "internal olefin" may refer to an ester or an acid thereof where R' denotes hydrogen or any organic compound (such as an alkyl, aryl, or silyl group) and R has an olefin positioned at an internal location on the chain.

As used herein, "acid" or "acids" refer to compounds having the general formula: R—COOH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "acids" may refer to a group of compounds with the general formula described above, wherein the compounds have different carbon lengths. The term "carboxyl" refers to a —COOH moiety.

As used herein, "carboxylate compound" or "carboxylate compounds" refer to compounds having the general formula: R—COO$^-$, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "carboxylate compounds" may refer to a group of compounds with the general formula described above, wherein the compounds have different carbon lengths. The term "carboxylate" refers to a —COO$^-$ moiety.

As used herein, the term "dibasic ester" may refer to compounds having the general formula R—OOC—Y—COO—R', wherein Y, R, and R' denote any organic compound (such as alkyl, aryl, or silyl groups), including those bearing heteroatom containing substituent groups. In certain embodiments, Y is a saturated or unsaturated hydrocarbon, and R and R' are alkyl or alkenyl groups. In instances where Y is a saturated hydrocarbon, the dibasic ester can be referred to as a "saturated dibasic ester." In instances where Y is an unsaturated hydrocarbon, the dibasic ester can be referred to as an "unsaturated dibasic ester."

As used herein, the term "dicarboxylate compound" may refer to compounds having the general formula $^-$OOC—Y—COO$^-$, wherein Y denotes any organic compound (such as an alkyl, aryl, or silyl group), including those bearing heteroatom substituent groups. In certain embodiments, Y is a saturated or unsaturated hydrocarbon. In instances where Y is a saturated hydrocarbon, the dibasic acid can be referred to as a "saturated dicarboxylate compound." In instances where Y is an unsaturated hydrocarbon, the dibasic acid can be referred to as an "unsaturated dicarboxylate compound."

As used herein, the term "dibasic acid" may refer to compounds having the general formula R—OOC—Y—COO—R', wherein R and R' are hydrogen atoms, and Y denotes any organic compound (such as an alkyl, aryl, or silyl group), including those bearing heteroatom substituent groups. In certain embodiments, Y is a saturated or unsaturated hydrocarbon. In instances where Y is a saturated hydrocarbon, the dibasic acid can be referred to as a "saturated dibasic acid." In instances where Y is an unsaturated hydrocarbon, the dibasic acid can be referred to as an "unsaturated dibasic acid."

As used herein, "alcohol" or "alcohols" refer to compounds having the general formula: R—OH, wherein R denotes any organic moiety (such as alkyl, aryl, or silyl groups), including those bearing heteroatom-containing substituent groups. In certain embodiments, R denotes alkyl, alkenyl, aryl, or alcohol groups. In certain embodiments, the term "alcohol" or "alcohols" may refer to a group of compounds with the general formula described above, wherein the compounds have different carbon lengths. The term "hydroxyl" refers to a —OH moiety.

As used herein, "alkyl" refers to a straight or branched chain saturated hydrocarbon having 1 to 30 carbon atoms, which may be optionally substituted, as herein further described, with multiple degrees of substitution being allowed. Examples of "alkyl," as used herein, include, but are not limited to, methyl, ethyl, n-propyl, isopropyl, isobutyl, n-butyl, sec-butyl, tert-butyl, isopentyl, n-pentyl, neopentyl, n-hexyl, and 2-ethylhexyl. The number of carbon atoms in an alkyl group is represented by the phrase "$C_{x-y}$ alkyl," which refers to an alkyl group, as herein defined, containing from x to y, inclusive, carbon atoms. Thus, "$C_{1-6}$ alkyl" represents an alkyl chain having from 1 to 6 carbon atoms and, for example, includes, but is not limited to, methyl, ethyl, n-propyl, isopropyl, isobutyl, n-butyl, sec-butyl, tert-butyl, isopentyl, n-pentyl, neopentyl, and n-hexyl. In some instances, the "alkyl" group can be divalent, in which case the group can alternatively be referred to as an "alkylene" group. Also, in some instances, one or more of the carbon atoms in the alkyl or alkylene group can be replaced by a heteroatom (e.g., selected from nitrogen, oxygen, or sulfur, including N-oxides, sulfur oxides, and sulfur dioxides, where feasible), and is referred to as a "heteroalkyl" or "heteroalkylene" group, respectively. Non-limiting examples include "oxyalkyl" or "oxyalkylene" groups, which are groups of the following formulas: -[-(alkylene)-O-]$_x$-alkyl, or -[-(alkylene)-O-]$_x$-alkylene-, respectively, where x is 1 or more, such as 1, 2, 3, 4, 5, 6, 7, or 8.

As used herein, "alkenyl" refers to a straight or branched chain non-aromatic hydrocarbon having 2 to 30 carbon atoms and having one or more carbon-carbon double bonds, which may be optionally substituted, as herein further described, with multiple degrees of substitution being allowed. Examples of "alkenyl," as used herein, include, but are not limited to, ethenyl, 2-propenyl, 2-butenyl, and 3-butenyl. The number of carbon atoms in an alkenyl group is represented by the phrase "$C_{x-y}$ alkenyl," which refers to an alkenyl group, as herein defined, containing from x to y, inclusive, carbon atoms. Thus, "$C_{2-6}$ alkenyl" represents an alkenyl chain having from 2 to 6 carbon atoms and, for example, includes, but is not limited to, ethenyl, 2-propenyl, 2-butenyl, and 3-butenyl. In some instances, the "alkenyl" group can be divalent, in which case the group can alternatively be referred to as an "alkenylene" group. Also, in some instances, one or more of the saturated carbon atoms in the alkenyl or alkenylene group can be replaced by a heteroatom (e.g., selected from nitrogen, oxygen, or sulfur, including N-oxides, sulfur oxides, and sulfur dioxides, where feasible), and is referred to as a "heteroalkenyl" or "heteroalkenylene" group, respectively.

As used herein, "alkynyl" refers to a straight or branched chain non-aromatic hydrocarbon having 2 to 30 carbon atoms and having one or more carbon-carbon triple bonds, which may be optionally substituted, as herein further described, with multiple degrees of substitution being allowed. Examples of "alkynyl," as used herein, include, but are not limited to, ethynyl, 2-propynyl, 2-butynyl, and 3-butynyl. The number of carbon atoms in an alkynyl group is represented by the phrase "$C_{x-y}$ alkynyl," which refers to an alkynyl group, as herein defined, containing from x to y, inclusive, carbon atoms. Thus, "$C_{2-6}$ alkynyl" represents an alkynyl chain having from 2 to 6 carbon atoms and, for example, includes, but is not limited to, ethynyl, 2-propynyl, 2-butynyl, and 3-butynyl. In some instances, the "alkynyl" group can be divalent, in which case the group can alternatively be referred to as an "alkynylene" group. Also, in some instances, one or more of the saturated carbon atoms in the alkynyl group can be replaced by a heteroatom (e.g., selected from nitrogen, oxygen, or sulfur, including N-oxides, sulfur oxides, and sulfur dioxides, where feasible), and is referred to as a "heteroalkynyl" group.

As used herein, "cycloalkyl" refers to an aliphatic saturated or unsaturated hydrocarbon ring system having 1 to 20 carbon atoms, which may be optionally substituted, as herein further described, with multiple degrees of substitution being allowed. Examples of "cycloalkyl," as used herein, include, but are not limited to, cyclopropyl, cyclobutyl, cyclopentyl, cyclohexyl, cyclohexenyl, cycloheptyl, cyclooctyl, adamantyl, and the like. The number of carbon atoms in an cycloalkyl group is represented by the phrase "$C_{x-y}$ alkyl," which refers to a cycloalkyl group, as herein defined, containing from x to y, inclusive, carbon atoms. Thus, "$C_{3-10}$ cycloalkyl" represents a cycloalkyl having from 3 to 10 carbon atoms and, for example, includes, but is not limited to, cyclopropyl, cyclobutyl, cyclopentyl, cyclohexyl, cyclohexenyl, cycloheptyl, cyclooctyl, and adamantyl. In some instances, the "cycloalkyl" group can be divalent, in which case the group can alternatively be referred to as a "cycloalkylene" group. Also, in some instances, one or more of the carbon atoms in the cycloalkyl or cycloalkylene group can be replaced by a heteroatom (e.g., selected from nitrogen, oxygen, or sulfur, including N-oxides, sulfur oxides, and sulfur dioxides, where feasible), and is referred to as a "heterocycloalkyl" or "heterocycloalkylene" group, respectively.

As used herein, "alkoxy" refers to —OR, where R is an alkyl group (as defined above). The number of carbon atoms in an alkyl group is represented by the phrase "$C_{x-y}$ alkoxy," which refers to an alkoxy group having an alkyl group, as herein defined, containing from x to y, inclusive, carbon atoms.

As used herein, "halogen" or "halo" refers to a fluorine, chlorine, bromine, and/or iodine atom. In some embodiments, the terms refer to fluorine and/or chlorine. As used herein, "haloalkyl" or "haloalkoxy" refer to alkyl or alkoxy groups, respectively, substituted by one or more halogen atoms. The terms "perfluoroalkyl" or "perfluoroalkoxy" refer to alkyl groups and alkoxy groups, respectively, where every available hydrogen is replaced by fluorine.

As used herein, "substituted" refers to substitution of one or more hydrogen atoms of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week. As used herein, the phrases "substituted with one or more . . . " or "substituted one or more times . . . " refer to a number of substituents that equals from one to the maximum number of substituents possible based on the number of available bonding sites, provided that the above conditions of stability and chemical feasibility are met.

As used herein, "yield" refers to the amount of reaction product formed in a reaction. When expressed with units of percent (%), the term yield refers to the amount of reaction product actually formed, as a percentage of the amount of reaction product that would be formed if all of the limiting reactant were converted into the product.

As used herein, "mix" or "mixed" or "mixture" refers broadly to any combining of two or more compositions. The two or more compositions need not have the same physical state; thus, solids can be "mixed" with liquids, e.g., to form a slurry, suspension, or solution. Further, these terms do not require any degree of homogeneity or uniformity of composition. This, such "mixtures" can be homogeneous or heterogeneous, or can be uniform or non-uniform. Further, the terms do not require the use of any particular equipment to carry out the mixing, such as an industrial mixer.

As used herein, "optionally" means that the subsequently described event(s) may or may not occur. In some embodiments, the optional event does not occur. In some other embodiments, the optional event does occur one or more times.

As used herein, "comprise" or "comprises" or "comprising" or "comprised of" refer to groups that are open, meaning that the group can include additional members in addition to those expressly recited. For example, the phrase, "comprises A" means that A must be present, but that other members can be present too. The terms "include," "have," and "composed of" and their grammatical variants have the same meaning. In contrast, "consist of" or "consists of" or "consisting of" refer to groups that are closed. For example, the phrase "consists of A" means that A and only A is present.

As used herein, "or" is to be given its broadest reasonable interpretation, and is not to be limited to an either/or construction. Thus, the phrase "comprising A or B" means that A can be present and not B, or that B is present and not A, or that A and B are both present. Further, if A, for example, defines a class that can have multiple members, e.g., $A_1$ and $A_2$, then one or more members of the class can be present concurrently.

As used herein, the various functional groups represented will be understood to have a point of attachment at the functional group having the hyphen or dash (-) or an asterisk (*). In other words, in the case of —$CH_2CH_2CH_3$, it will be understood that the point of attachment is the $CH_2$ group at the far left. If a group is recited without an asterisk or a dash, then the attachment point is indicated by the plain and ordinary meaning of the recited group.

As used herein, multi-atom bivalent species are to be read from left to right. For example, if the specification or claims recite A-D-E and D is defined as —OC(O)—, the resulting group with D replaced is: A-OC(O)-E and not A-C(O)O-E.

Other terms are defined in other portions of this description, even though not included in this subsection.

Saponification of Dibasic Esters

In certain aspects, the disclosure provides methods for saponifying a dibasic ester, comprising: introducing a dibasic ester to a reactor; and saponifying the dibasic ester to form a dicarboxylate compound.

The methods include introducing a dibasic ester to a reactor. The acid can be introduced in any suitable manner. For example, in some embodiments, the dibasic ester is added to the reactor, either alone or with other ingredients. In some other embodiments, however, the dibasic acid is generated in the reactor, for example, as the product of a chemical reaction that occurs in the reactor. The dibasic ester can be in any suitable form, for example, as a solid, in a slurry with a suitable liquid carrier, in a suspension with a suitable liquid carrier, or dissolved in a solvent. In some embodiments, the dibasic acid is introduced to the reactor as a solid composition. In some other embodiments, the dibasic ester is introduced to the reactor dissolved in a solution. Any suitable solvent system can be used for the solution, including, but not limited to, solvent systems that include ethyl acetate, acetonitrile, heptane, hexane, diethyl ether, methyl tert-butyl ether (MBTE), petroleum ether, toluene, ortho-xylene, meta-xylene, para-xylene, acetone, dimethylformamide, tetrahydrofuran, methylene dichloride, 1-butanol, isopropyl alcohol, isopropyl acetate, 1,2-dimethoxyethane, and dimethyl sulfoxide. In some embodiments, the solvent system comprises toluene. In some embodiments, these solvent systems can include compounds that are miscible with water. In some embodiments, these solvent systems can include compounds that are not miscible with water. In some embodiments, these solvent systems can include one or more compounds that are not miscible with water and one or more compounds that are miscible in water.

In some embodiments, the composition can also include other organic esters, such as monobasic esters, but in smaller relative quantities than the dibasic ester. In some embodiments, these monobasic esters can include esters of various saturated fatty acids. These include, but are not limited to, esters of hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, and the like. In some embodiments, these monobasic esters can include esters of various unsaturated fatty acids, such as esters of octenoic acid, nonenoic acid, decenoic acid, undecenoic acid, dodecenoic acid, tridecenoic acid, tetradecenoic acid, pentadecenoic acid, hexadecenoic acid, heptadecenoic acid, octadecenoic acid, tridecadienoic acid, hexadecadienoic acid, and the like. In some embodiments, such esters are esters of simple aliphatic alcohols, such as methyl esters, ethyl esters, or isopropyl esters, of any of the aforementioned acids.

In some embodiments, the dibasic ester can be formed by a process that includes self-metathesizing an unsaturated ester or cross-metathesizing two or more unsaturated esters. In such embodiments, the composition can include small quantities of the saturated (e.g., hydrogenated) variants of the unsaturated esters used as reactants in the metathesis. The composition can also include other saturated (e.g., hydrogenated) mono-ester byproducts of the metathesis reaction, e.g., from the non-productive metathesis of the reactants with various alkenes and olefinic esters formed in the metathesis reactor.

In some embodiments, the dibasic ester is disposed in the reactor as a component of a composition. In some embodiments, the composition also includes water or a substance that can release water. In some embodiments, the dibasic ester is disposed in a composition that comprises water. In some such embodiments, the dibasic ester is suspended in the water. In some other embodiments, the dibasic ester is slurried in the water.

In certain aspects, the methods include saponifying the dibasic ester to form a dicarboxylate compound. The saponification can be carried out in any suitable medium. In some embodiments, the reaction medium comprises water, e.g., is an aqueous medium. In some such embodiments, the reaction medium is at least 50 percent by weight, or at least 60 percent by weight, or at least 70 percent by weight, or at least 80 percent by weight, or at least 90 percent by weight water, based on the total weight of solvent medium present.

In some embodiments, the saponifying comprises reacting the dibasic ester with a base, such as a water soluble base. Any suitable base can be used. In some embodiments, the base includes an alkali metal hydroxide, an alkaline earth metal hydroxide, an alkali metal $C_{1-4}$ alkoxide, an alkaline earth metal $C_{1-4}$ alkoxide, or any combinations thereof. In some such embodiments, the base includes an alkali metal hydroxide, an alkaline earth metal hydroxide, or any combinations thereof. In some further embodiments, the base includes sodium hydroxide, potassium hydroxide, magnesium hydroxide, calcium hydroxide, or any combinations thereof. In some further embodiments, the base includes sodium hydroxide, potassium hydroxide, or any combinations thereof. In some embodiments, the base includes sodium hydroxide. In some other embodiments, the base includes potassium hydroxide. Further, in any of the aforementioned embodiments, one or more of those bases can be homogeneous, meaning that they are at least partially solubilized by a liquid carrier (e.g., an aqueous carrier). In some other embodiments, however, one or more of the bases are heterogeneous, meaning that they are not solubilized by any liquid carrier. For example, in some such embodiments, one or more of the bases can be disposed on a solid support, such as a polymeric support (e.g., polystyrene and the like) or an inorganic support (e.g., silica, alumina, and the like).

The method is not limited to any particular dibasic ester. In some embodiments, the dibasic ester is a compound having the formula: R—OOC—Y—COO—R', wherein Y, R, and R' denote any organic compound (such as hydrocarbyl or silyl groups), including those bearing heteroatom containing substituent groups. In some such embodiments, R and R' are independently hydrocarbyl groups, which can be optionally substituted with various heteroatom-containing substituents, or whose carbon atoms can be replaced by one or more heteroatoms. Such hydrocarbyl groups can include substituted and unsubstituted alkyl, alkenyl, and oxyalkyl groups. In some such embodiments, Y is a divalent hydrocarbyl group, which can be optionally substituted with various heteroatom-containing substituents, or whose carbon atoms can be replaced by one or more heteroatoms. Such divalent hydrocarbyl groups can include substituted and unsubstituted alkylene, alkenylene, and oxyalkylene groups.

In some embodiments, the dibasic ester is a compound of formula (I):

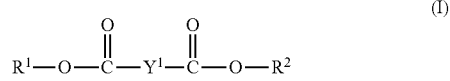

(I)

wherein, $Y^1$ is $C_{6-36}$ alkylene, $C_{6-36}$ alkenylene, $C_{6-36}$ heteroalkylene, or $C_{6-36}$ heteroalkenylene, each of which is optionally substituted one or more times by substituents selected independently from $R^3$;

$R^1$ and $R^2$ are independently $C_{1-12}$ alkyl, $C_{1-12}$ heteroalkyl, $C_{2-12}$ alkenyl, or $C_{2-12}$ heteroalkenyl, each of which is optionally substituted one or more times by substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$ alkylene, $C_{6-36}$ alkenylene, or $C_{4-36}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and —N($C_{1-6}$ alkyl)$_2$. In some further such embodiments, $Y^1$ is $C_{6-36}$ alkylene, $C_{6-36}$ alkenylene, or $C_{4-36}$ oxyalkylene, each of which is optionally substituted one or more times by —OH. In some further such embodiments, $Y^1$ is —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{20}$—, —(CH$_2$)$_{21}$—, or —(CH$_2$)$_{22}$—. In some embodiments, $Y^1$ is —(CH$_2$)$_9$—. In some embodiments, $Y^1$ is —(CH$_2$)$_{12}$—. In some embodiments, $Y^1$ is —(CH$_2$)$_{16}$—.

In some embodiments, $R^1$ and $R^2$ are independently $C_{1-8}$ alkyl, $C_{2-8}$ alkenyl, or $C_{1-8}$ oxyalkenyl, each of which is optionally substituted one or more times by —OH. In some further embodiments, $R^1$ and $R^2$ are independently methyl, ethyl, propyl, isopropyl, butyl, isobutyl, sec-butyl, tert-butyl, pentyl, tert-pentyl, neopentyl, hexyl, or 2-ethylhexyl. In some further embodiments, $R^1$ and $R^2$ are independently methyl, ethyl, or isopropyl. In some embodiments, $R^1$ and $R^2$ are both methyl.

In some embodiments, the dibasic ester is undecanedioic acid dimethyl ester. In some embodiments, the dibasic ester is tetradecanedioic acid dimethyl ester. In some embodiments, the dibasic ester is octadecanedioic acid dimethyl ester.

Any suitable amount of the dibasic ester can be disposed in the reactor. In some embodiments, at least 50 grams, or at least 100 grams, or at least 150 grams, or at least 200 grams, are introduced to the reactor.

Any suitable reactor can be used for introducing the dibasic ester. In some embodiments, the reactor is a pressurizable reactor. In some such embodiments, the reactor includes a sealable reaction vessel that can hold a pressure up to about 5 bar, or up to about 10 bar, or up to about 20 bar, or up to about 30 bar, or up to about 40 bar, or up to about 50 bar, or up to about 75 bar, or up to about 100 bar. In some embodiments, the reactor is equipped with a means of heating its contents. Thus, in some embodiments, the reactor can include one or more heating elements disposed proximate to the reaction vessel. Any suitable heating elements can be used, including, but not limited to, electric wires (e.g., electric heating coils), thermocouples, gas burners, heating blocks, pipes containing heated fluids (e.g., steam pipes, hot oil pipes, etc.), and the like. In some embodiments, one or more suitable heating elements can be included on the inside of the reaction vessel. In some embodiments, such internal heating elements can be the sole means used for heating the reactor contents. In other embodiments, however, such internal heating elements can be used in addition to one or more external heating elements. Because such internal heating elements may be in contact with the reactor contents, in some embodiments, the internal heating element is designed such that it can operate when in physical contact with one or more of the reactor contents. For example, in some embodiments, such internal heating elements include, but are not limited to, electric wires (e.g., electric heating coils), thermocouples, pipes containing heated fluids (e.g., steam pipes, hot oil pipes, etc.), and the like.

The reaction vessel can have any suitable volume and/or shape, depending on the certain factors, including, but not limited to, the nature of the reactants and products, the desired reaction temperature and pressure, the quantities of reactants. In some embodiments, the reaction vessel is a 600 mL Hastelloy C Parr reactor. In some other embodiments, the reaction vessel is a Hastelloy C pressure reactor, e.g., having a volume of 500 L to 9000 L.

In some embodiments, the reaction vessel can include various devices or structures to assist with fluid flow. Such devices or structures can include, but are not limited to, baffles, stirrers, stir bars, impellers, and the like. These elements can be disposed in the reactor in any suitable manner, depending on the desired reaction conditions, the nature of the reactor contents, and on other factors.

The reactor can also include various inlets and outlets for adding or removing fluids (including gases and/or liquids) from the reactor. In some embodiments, the reactor includes an inlet suitable for adding a liquid medium to the reactor. In some such embodiments, this liquid inlet is in fluid communication with a vessel containing said liquid medium. In some such embodiments, one or more pumps can be disposed between the liquid-containing vessel and the inlet. Any pumps suitable for pumping a liquid medium can be used. In some embodiments, the liquid medium is an aqueous medium, such as water. In some embodiments, the reactor includes an outlet suitable for removing a gaseous medium from the reaction vessel. In some embodiments, said gas outlet is in fluid communication with a receiving vessel. In some embodiments, the receiving vessel is a condenser, or is disposed proximate to one or more cooling elements, such that one or more of the substances contained in any gaseous stream can be condensed to a liquid. In some such embodiments, one or more pressure regulators are disposed between the receiving vessel and the gaseous outlet. Any suitable regulators can be used, so long as they can allow release of one or more gaseous species from the reactor without inducing a substantial reduction of reactor pressure. In some embodiments, the reactor may also include a gaseous inlet, such as a gaseous inlet that can be used for adding one or more gases (e.g., inert gases or non-reacting gases) to the reactor. Such an inlet can be used to sparge the reactor, e.g., during the course of the reaction. Or, in some other instances, it can be used to flush the reactor of undesired species, e.g., to flush the reactor of oxidants, such as oxygen. In some embodiments, the gas inlet is suitable for delivery of certain inert gases to the reactor, either before, during, and/or after the reaction. Such inert gases include, but are not limited to, nitrogen, helium, neon, argon, methane (flared), carbon dioxide, and the like.

The methods include reacting the dibasic ester with water in the reactor to form a dicarboxylate compound (i.e., a dicarboxylate di-anion). Accordingly, in some embodiments, the resulting dibasic acid is a compound having the formula: $^-$OOC—Y—COO$^-$, wherein Y denotes any organic compound (such as hydrocarbyl or silyl groups), including those bearing heteroatom containing substituent groups. In some such embodiments, Y is a divalent hydrocarbyl group, which can be optionally substituted with various heteroatom-containing substituents, or whose carbon atoms can be replaced by one or more heteroatoms. Such divalent hydrocarbyl groups can include substituted and unsubstituted alkylene, alkenylene, and oxyalkylene groups.

In some embodiments, the reaction forms a dicarboxylate compound of formula (II):

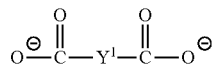

(II)

wherein, $Y^1$ is $C_{6-36}$ alkylene, $C_{6-36}$ alkenylene, $C_{6-36}$ heteroalkylene, or $C_{6-36}$ heteroalkenylene, each of which is optionally substituted one or more times by substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$ alkylene, $C_{6-36}$ alkenylene, or $C_{4-36}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and N($C_{1-6}$ alkyl)$_2$. In some further such embodiments, $Y^1$ is $C_{6-36}$ alkylene, $C_{6-36}$ alkenylene, or $C_{4-36}$ oxyalkylene, each of which is optionally substituted one or more times by —OH. In some further such embodiments, $Y^1$ is —(CH$_2$)$_8$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{29}$—, —(CH$_2$)$_{21}$—, or —(CH$_2$)$_{22}$—. In some embodiments, $Y^1$ is —(CH$_2$)$_9$—. In some embodiments, $Y^1$ is —(CH$_2$)$_{12}$—. In some embodiments, $Y^1$ is —(CH$_2$)$_{16}$—.

In some embodiments, the dicarboxylate compound is undecanedioate. In some embodiments, the dicarboxylate compound is tetradecanedioate. In some embodiments, the dicarboxylate compound is octadecanedioate acid.

In some embodiments, the methods include acidifying the dicarboxylate compound (according to any of the above embodiments) to form a dibasic acid. The acidifying comprises reacting the dicarboxylate compound with an acid, such as a water soluble base. Any suitable acid can be used. In some embodiments, the acid includes hydrochloric acid. Further, in any of the aforementioned embodiments, one or more of those acids can be homogeneous, meaning that they are at least partially solubilized by a liquid carrier (e.g., an aqueous carrier). In some other embodiments, however, one or more of the acids are heterogeneous, meaning that they are not solubilized by any liquid carrier. For example, in some such embodiments, one or more of the acids can be disposed on a solid support, such as a polymeric support (e.g., polystyrene and the like) or an inorganic support (e.g., silica, alumina, and the like).

The dicarboxylate compound can be a dicarboxylate compound according to any of the above embodiments. Accordingly, in some embodiments, the resulting dibasic acid is a compound having the formula: H—OOC—Y—COO—H, wherein Y denotes any organic compound (such as hydrocarbyl or silyl groups), including those bearing heteroatom containing substituent groups. In some such embodiments, Y is a divalent hydrocarbyl group, which can be optionally substituted with various heteroatom-containing substituents, or whose carbon atoms can be replaced by one or more heteroatoms. Such divalent hydrocarbyl groups can include substituted and unsubstituted alkylene, alkenylene, and oxyalkylene groups. In some such embodiments, the reaction also yields one or more alcohols. In some embodiments, the alcohols are compounds having the formulas: R—OH and R'—OH, where R and R' denote any organic compound (such as hydrocarbyl or silyl groups), including those bearing heteroatom containing substituent groups. In some such embodiments, R and R' are independently hydrocarbyl groups, which can be optionally substituted with various heteroatom-containing substituents, or whose carbon atoms can be replaced by one or more heteroatoms. Such hydrocarbyl groups can include substituted and unsubstituted alkyl, alkenyl, and oxyalkyl groups.

In some embodiments, the reaction forms a dibasic acid of formula (II) and alcohols of formula (IIIa) and formula (IIIb):

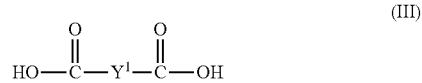

(III)

wherein, $Y^1$ is $C_{6-36}$ alkylene, $C_{6-36}$ alkenylene, $C_{6-36}$ heteroalkylene, or $C_{6-36}$ heteroalkenylene, each of which is optionally substituted one or more times by substituents selected independently from $R^3$; and $R^3$ is a halogen atom, —OH, —NH$_2$, $C_{1-6}$ alkyl, $C_{1-6}$ heteroalkyl, $C_{2-6}$ alkenyl, $C_{2-6}$ heteroalkenyl, $C_{3-10}$ cycloalkyl, or $C_{2-10}$ heterocycloalkyl.

In some embodiments, $Y^1$ is $C_{6-36}$ alkylene, $C_{6-36}$ alkenylene, or $C_{4-36}$ oxyalkylene, each of which is optionally substituted one or more times by substituents selected from the group consisting of a halogen atom, —OH, —O($C_{1-6}$ alkyl), —NH$_2$, —NH($C_{1-6}$ alkyl), and N($C_{1-6}$ alkyl)$_2$. In some further such embodiments, $Y^1$ is $C_{6-36}$ alkylene, $C_{6-36}$ alkenylene, or $C_{4-36}$ oxyalkylene, each of which is optionally substituted one or more times by —OH. In some further such embodiments, $Y^1$ is —(CH$_2$)$_8$—, —(CH$_2$)$_9$—, —(CH$_2$)$_9$—, —(CH$_2$)$_{10}$—, —(CH$_2$)$_{11}$—, —(CH$_2$)$_{12}$—, —(CH$_2$)$_{13}$—, —(CH$_2$)$_{14}$—, —(CH$_2$)$_{15}$—, —(CH$_2$)$_{16}$—, —(CH$_2$)$_{17}$—, —(CH$_2$)$_{18}$—, —(CH$_2$)$_{19}$—, —(CH$_2$)$_{20}$—, —(CH$_2$)$_{21}$—, or —(CH$_2$)$_{22}$—. In some embodiments, $Y^1$ is —(CH$_2$)$_9$—. In some embodiments, $Y^1$ is —(CH$_2$)$_{12}$—. In some embodiments, $Y^1$ is —(CH$_2$)$_{16}$—.

In some embodiments, the dibasic acid is undecanedioic acid. In some embodiments, the dibasic acid is tetradecanedioic acid. In some embodiments, the dibasic acid is octadecanedioic acid.

In some embodiments, the dibasic acid may be subjected to additional purification, for example, using any of the embodiments of the purification methods described below. In some other embodiments, however, such additional purification may be unnecessary.

In some embodiments, the methods described herein can lead to relatively high conversion percentages, e.g., the percentage of dibasic ester converted to dibasic acid. In some embodiments, at least 75%, or at least 80%, or at least 90%, or at least 95%, or at least 97%, or at least 99%, of the dibasic ester is converted to dibasic acid within the duration of the reaction. Further, in some embodiments, the amount of dibasic ester converted to a dibasic monoacid/monoester (e.g., a dibasic ester which reacts in such a way that, in the product, only one of the two ester groups has been converted to an acid). Thus, in some embodiments, the mole-to-mole ratio of dibasic acid to dibasic monoacid/monoester in the product is at least 25:1, or at least 35:1, or at least 50:1, or at least 100:1, or at least 200:1, or at least 300:1.

Once the dibasic acid is obtained in the desired purity, the solid can be dried. Any suitable drying technique can be used. For example, in some embodiments, the sample is dried in a drying unit, such as a rotary dryer. The dried material can be packaged in any suitable form, including, but not limited to, pellets, flakes, pastels, and the like.

FIG. 1 shows an illustrative embodiment of a method for saponifying a dibasic ester to a dicarboxylate compound. The method 100 includes: introducing a dibasic ester to a reactor 101; and saponifying the dibasic ester 102 to form a dicarboxylate compound.

Figure 2:
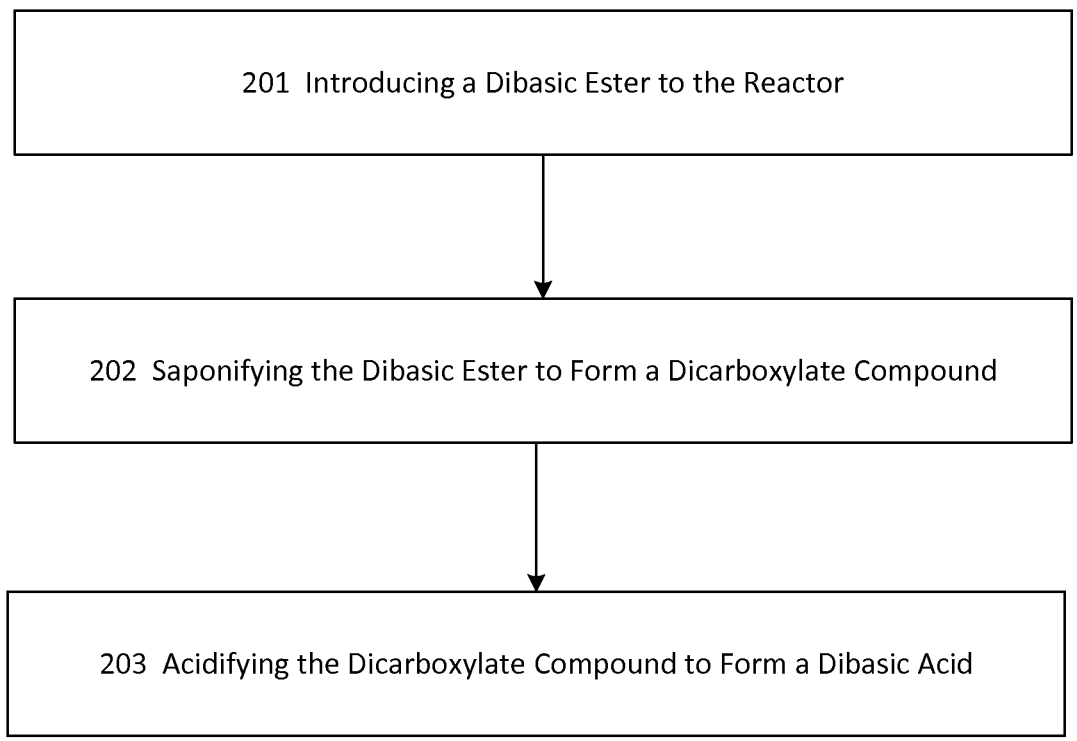
FIG. 2 shows an illustrative embodiment of a method for saponifying a dibasic ester to form a dibasic acid.

FIG. 2 shows an illustrative embodiment of a method for saponifying a dibasic ester to a dibasic acid. The method 200 includes: introducing a dibasic ester to a reactor 201; saponifying the dibasic ester 202 to form a dicarboxylate compound; and acidifying the dicarboxylate compound 203 to form a dibasic acid. In some embodiments, the mole-to-mole ratio of formed dibasic acid to colored impurities is at least 250:1.

Purifying a Dibasic Acid Composition

In certain aspects, the disclosure provides methods of forming a purified solid-state dibasic acid composition. In such embodiments, the dibasic acid resulting from any of the aforementioned embodiments is purified. In some embodiments, the purification includes disposing the dibasic acid in a system having two or more phases, include an aqueous phase and an organic phase. In some embodiments, the dibasic acid is already disposed in an aqueous medium following acidification. Therefore, in some such embodiments, the multi-phase solution is obtained by adding an organic solvent to the aqueous composition containing the dibasic acid. Any suitable organic solvent can be used. It is desirable, however, that the organic solvent be capable of dissolving the dibasic acid without the use of extreme conditions. Suitable organic solvents include, but are not limited to, solvents comprising toluene, ortho-xylene, meta-xylene, para-xylene, acetone, dimethylformamide, tetrahydrofuran, methylene dichloride, dimethyl sulfoxide, or any mixture thereof. In some embodiments, the organic solvent comprises toluene, ortho-xylene, meta-xylene, para-xylene, or any mixtures thereof. In some further embodiments, the organic solvent comprises toluene. In some such embodiments, the organic solvent is predominantly toluene, e.g., at least 50% by volume, or at least 70% by volume, or at least 80% by volume, or at least 90% by volume toluene, based on the total volume of organic solvent added.

In some embodiments, the organic solvent is at an elevated temperature in the multi-phase composition. This can be achieved in any suitable manner. In some embodiments, the organic solvent is heated prior to addition to the aqueous composition. In some embodiments, the organic solvent is at a temperature of at least 60° C. or at least 70° C., up to 90° C. or up to 100° C. Any suitable amount of the organic solvent can be used relative to the aqueous composition. In some embodiments, the volume-to-volume ratio of organic solvent to water is at least 5:1, or at least 7:1, up to 10:1 or up to 20:1.

In some embodiments, the dibasic acid is recrystallized out of the organic phase by cooling. In some embodiments, the organic phase and the aqueous phase are separated. In some embodiments, the organic phase is washed with an aqueous medium (e.g., water) one or more times to remove further impurities, such as sodium or potassium cations from the base. In some embodiments, the organic phase, which is optionally separated and/or washed, is cooled to a temperature of no more than 50° C. or no more than 40° C. or no more than 35° C., down to 0° C. or down to 10° C., or down to 20° C., or down to 25° C.

Figure 3:
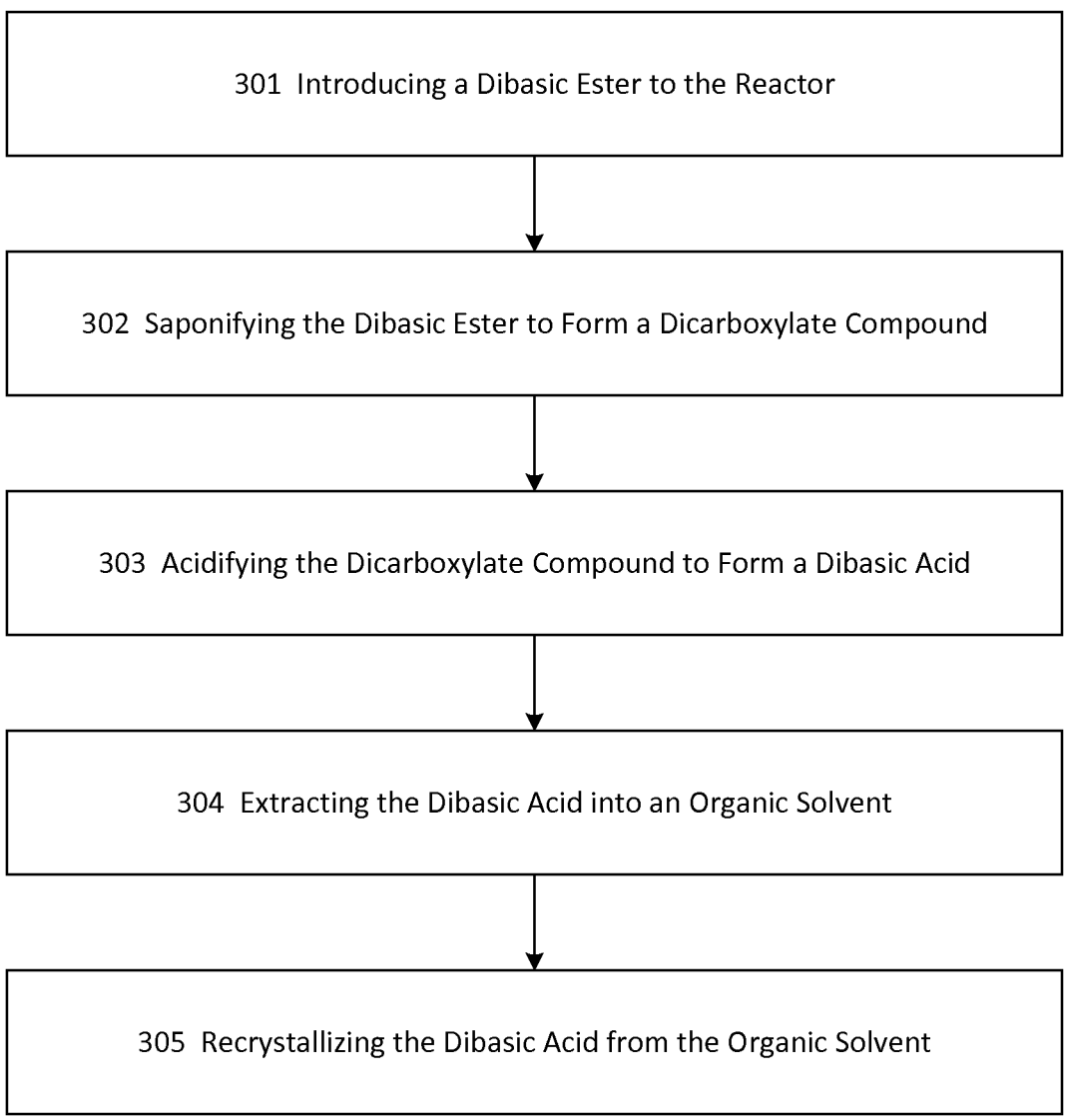
FIG. 3 shows an illustrative embodiments for forming a purified solid-state dibasic acid composition.

FIG. 3 shows an illustrative embodiments for forming a purified solid-state dibasic acid composition. The method 300 includes: introducing a dibasic ester to a reactor 301; saponifying the dibasic ester 302 to form a dicarboxylate compound; acidifying the dicarboxylate compound 303 to form a dibasic acid; extracting the dibasic acid into an organic solvent 304; and recrystallizing the dibasic acid from the organic solvent 305.

Dibasic Esters by Metathesis

The dibasic esters disclosed herein can be formed by any suitable means. In some embodiments, the dibasic esters are formed by metathesis. Reactions of olefinic esters to make unsaturated dibasic esters are generally described in PCT Publication No. WO 2008/140468, and United States Patent Application Publication Nos. 2009/0264672 and 2013/0085288, all three of which are hereby incorporated by reference as though fully set forth herein in their entireties. In some embodiments, the resulting unsaturated dibasic esters can be saturated by hydrogenation to form saturated dibasic esters.

Derivation from Renewable Sources

The dibasic esters employed in any of the above aspects and embodiments can, in certain embodiments, be derived from renewable sources, such as various natural oils. Any suitable methods can be used to make these compounds from such renewable sources. Suitable methods include, but are not limited to, fermentation, conversion by bioorganisms, and conversion by metathesis.

Olefin metathesis provides one possible means to convert certain natural oil feedstocks into olefins and esters that can be used in a variety of applications, or that can be further modified chemically and used in a variety of applications. In some embodiments, a composition (or components of a composition) may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical properties.

A wide range of natural oils, or derivatives thereof, can be used in such metathesis reactions. Examples of suitable natural oils include, but are not limited to, vegetable oils, algae oils, fish oils, animal fats, tall oils, derivatives of these oils, combinations of any of these oils, and the like. Representative non-limiting examples of vegetable oils include rapeseed oil (canola oil), coconut oil, corn oil, cottonseed oil, olive oil, palm oil, peanut oil, safflower oil, sesame oil, soybean oil, sunflower oil, linseed oil, palm kernel oil, tung oil, jatropha oil, mustard seed oil, pennycress oil, camelina oil, hempseed oil, and castor oil. Representative non-limiting examples of animal fats include lard, tallow, poultry fat, yellow grease, and fish oil. Tall oils are by-products of wood pulp manufacture. In some embodiments, the natural oil or natural oil feedstock comprises one or more unsaturated glycerides (e.g., unsaturated triglycerides). In some such embodiments, the natural oil feedstock comprises at least 50% by weight, or at least 60% by weight, or at least 70% by weight, or at least 80% by weight, or at least 90% by weight, or at least 95% by weight, or at least 97% by weight, or at least 99% by weight of one or more unsaturated triglycerides, based on the total weight of the natural oil feedstock.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

Metathesized natural oils can also be used. Examples of metathesized natural oils include but are not limited to a metathesized vegetable oil, a metathesized algal oil, a metathesized animal fat, a metathesized tall oil, a metathesized derivatives of these oils, or mixtures thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Such natural oils, or derivatives thereof, can contain esters, such as triglycerides, of various unsaturated fatty acids. The identity and concentration of such fatty acids varies depending on the oil source, and, in some cases, on the variety. In some embodiments, the natural oil comprises one or more esters of oleic acid, linoleic acid, linolenic acid, or any combination thereof. When such fatty acid esters are metathesized, new compounds are formed. For example, in embodiments where the metathesis uses certain short-chain olefins, e.g., ethylene, propylene, or 1-butene, and where the natural oil includes esters of oleic acid, an amount of 1-decene, among other products, is formed. Following transesterification, for example, with an alkyl alcohol, an amount of 9-denenoic acid methyl ester is formed. In some such embodiments, a separation step may occur between the metathesis and the transesterification, where the alkenes are separated from the esters. In some other embodiments, transesterification can occur before metathesis, and the metathesis is performed on the transesterified product.

In some embodiments, the natural oil can be subjected to various pre-treatment processes, which can facilitate their utility for use in certain metathesis reactions. Useful pre-treatment methods are described in United States Patent Application Publication Nos. 2011/0113679, 2014/0275681, and 2014/0275595, all three of which are hereby incorporated by reference as though fully set forth herein.

In some embodiments, after any optional pre-treatment of the natural oil feedstock, the natural oil feedstock is reacted in the presence of a metathesis catalyst in a metathesis reactor. In some other embodiments, an unsaturated ester (e.g., an unsaturated glyceride, such as an unsaturated triglyceride) is reacted in the presence of a metathesis catalyst in a metathesis reactor. These unsaturated esters may be a component of a natural oil feedstock, or may be derived from other sources, e.g., from esters generated in earlier-performed metathesis reactions. In certain embodiments, in the presence of a metathesis catalyst, the natural oil or unsaturated ester can undergo a self-metathesis reaction with itself. In other embodiments, the natural oil or unsaturated ester undergoes a cross-metathesis reaction with the low-molecular-weight olefin or mid-weight olefin. The self-metathesis and/or cross-metathesis reactions form a metathesized product wherein the metathesized product comprises olefins and esters.

In some embodiments, the low-molecular-weight olefin is in the $C_{2-6}$ range. As a non-limiting example, in one embodiment, the low-molecular-weight olefin may comprise at least one of: ethylene, propylene, 1-butene, 2-butene, isobutene, 1-pentene, 2-pentene, 3-pentene, 2-methyl-1-butene, 2-methyl-2-butene, 3-methyl-1-butene, cyclopentene, 1,4-pentadiene, 1-hexene, 2-hexene, 3-hexene, 4-hexene, 2-methyl-1-pentene, 3-methyl-1-pentene, 4-methyl-1-pentene, 2-methyl-2-pentene, 3-methyl-2-pentene, 4-methyl-2-pentene, 2-methyl-3-pentene, and cyclohexene. In some instances, a higher-molecular-weight olefin can also be used.

In some embodiments, the metathesis comprises reacting a natural oil feedstock (or another unsaturated ester) in the presence of a metathesis catalyst. In some such embodiments, the metathesis comprises reacting one or more unsaturated glycerides (e.g., unsaturated triglycerides) in the natural oil feedstock in the presence of a metathesis catalyst. In some embodiments, the unsaturated glyceride comprises one or more esters of oleic acid, linoleic acid, linoleic acid, or combinations thereof. In some other embodiments, the unsaturated glyceride is the product of the partial hydrogenation and/or the metathesis of another unsaturated glyceride (as described above). In some such embodiments, the metathesis is a cross-metathesis of any of the aforementioned unsaturated triglyceride species with another olefin, e.g., an alkene. In some such embodiments, the alkene used in the cross-metathesis is a lower alkene, such as ethylene, propylene, 1-butene, 2-butene, etc. In some embodiments, the alkene is ethylene. In some other embodiments, the alkene is propylene. In some further embodiments, the alkene is 1-butene. And in some even further embodiments, the alkene is 2-butene.

Metathesis reactions can provide a variety of useful products, when employed in the methods disclosed herein. For example, terminal olefins and internal olefins may be derived from a natural oil feedstock, in addition to other valuable compositions. Moreover, in some embodiments, a number of valuable compositions can be targeted through the self-metathesis reaction of a natural oil feedstock, or the cross-metathesis reaction of the natural oil feedstock with a low-molecular-weight olefin or mid-weight olefin, in the presence of a metathesis catalyst. Such valuable compositions can include fuel compositions, detergents, surfactants, and other specialty chemicals. Additionally, transesterified products (i.e., the products formed from transesterifying an ester in the presence of an alcohol) may also be targeted, non-limiting examples of which include: fatty acid methyl esters ("FAMEs"); biodiesel; 9-decenoic acid ("9DA") esters, 9-undecenoic acid ("9UDA") esters, and/or 9-dodecenoic acid ("9DDA") esters; 9DA, 9UDA, and/or 9DDA; alkali metal salts and alkaline earth metal salts of 9DA, 9UDA, and/or 9DDA; dimers of the transesterified products; and mixtures thereof.

Further, in some embodiments, the methods disclosed herein can employ multiple methathesis reactions. In some embodiments, the multiple metathesis reactions occur sequentially in the same reactor. For example, a glyceride containing linoleic acid can be metathesized with a terminal lower alkene (e.g., ethylene, propylene, 1-butene, and the like) to form 1,4-decadiene, which can be metathesized a second time with a terminal lower alkene to form 1,4-pentadiene. In other embodiments, however, the multiple metathesis reactions are not sequential, such that at least one other step (e.g., transesterification, hydrogenation, etc.) can be performed between the first metathesis step and the following metathesis step. These multiple metathesis procedures can be used to obtain products that may not be readily obtainable from a single metathesis reaction using available starting materials. For example, in some embodiments, multiple metathesis can involve self-metathesis followed by cross-metathesis to obtain metathesis dimers, trimmers, and the like. In some other embodiments, multiple metathesis can be used to obtain olefin and/or ester components that have chain lengths that may not be achievable from a single metathesis reaction with a natural oil triglyceride and typical lower alkenes (e.g., ethylene, propylene, 1-butene, 2-butene, and the like). Such multiple metathesis can be useful in an industrial-scale reactor, where it may be easier to perform multiple metathesis than to modify the reactor to use a different alkene.

The conditions for such metathesis reactions, and the reactor design, and suitable catalysts are as described above with reference to the metathesis of the olefin esters. That discussion is incorporated by reference as though fully set forth herein.

In the embodiments above, the natural oil (e.g., as a glyceride) is metathesized, followed by transesterification. In some other embodiments, transesterification can precede metathesis, such that the fatty acid esters subjected to metathesis are fatty acid esters of monohydric alcohols, such as methanol, ethanol, or isopropanol.

EXAMPLES

Example 1—Saponification, Acidification, and Purification of 1,18-Octadecanedioic Acid Dimethyl Ester (ODDAME) to Form 1,18-Octadecanedioic Acid (ODDA)

The ODDA is produced in the following processing steps. Crude ODDAME was stripped under vacuum (i.e., pressure less than 25 mmHg) at a temperature of about 500° F. to remove the low-boiling substances (lower-weight fatty acid methyl esters). The stripped ODDAME was then reacted with aqueous potassium hydroxide. To achieve conversion into ODDA, the mixture was heated to 302° F. and held for 6 hours. The reaction mixture will then be cooled to 200° F. and toluene and muriatic acid will be added. Additional toluene was added and muriatic acid was added to achieve a 1:1 molar ratio. The resulting material was then washed several times with 5% HCl/water, which served to acidify the dicarboxylate and to remove any residual potassium cation.

The resulting ODDA was then decolorized using activated carbon in an organic solvent (toluene). The purpose of this step is to remove colored bodies formed during the above reaction. The resulting sample was filtered via a sparkler filter and 0.25 micron cuno filter. Crystallization of ODDA from toluene was completed by slowly cooling the ODDA in a toluene solution from the filtration temperature (212° F.) to 68° F. Unreacted ODDAME and monoacid impurities will remain soluble in toluene at 68° F. while the bulk of the ODDA and other difunctional acids will precipitate out of solution for recovery as a crystalline solid. The toluene loading of 6.2 times is preferred. Recovery of the finished ODDA was completed using a Rosenmund filter.

Results are reported in Table 1. As used herein, the "Conversion %" is a molar percent and is: $100*\{[2X_{ODDAME}+X_{ODDA(H)ME}]_{initial}-[2X_{ODDAME}+X_{ODDA(H)ME}]_{final}\}/[2X_{ODDAME}+X_{ODDA(H)ME}]_{initial}$, where ODDAME refers to 1,18-octadecanedioic acid dimethyl ester, ODDA(H)ME refers to 1,18-octadecanedioic acid monomethyl ester, and $X_{ODDAME}$ and $X_{ODDA(H)ME}$ refer to the mole fraction of ODDAME and ODDA(H)ME, respectively. As used herein, "ODDA Yield %" is a molar percent and is: $100*X_{ODDA}/[X_{ODDA}+X_{ODDAME}+X_{ODDA(H)ME}]$, where $X_{ODDA}$ is the mole fraction of ODDA, and the other terms have the meanings as defined above. As used herein, "ODDA(H)ME Yield %" is a molar percent and is: $100*X_{ODDA(H)ME}/[X_{ODDA}+X_{ODDAME}+X_{ODDA(H)ME}]$, where the terms have the meanings as defined above. As used herein, the "Overall Water:Oil Molar Ratio" is $Z*[(mass of water initially)+(mass of water added during reaction)/(mass of water initially)]$, where Z is 10 for a 10:1 initial water-to-oil molar ratio, and is 40 for a 40:1 initial water-to-oil molar ratio.

TABLE 1

| | Example 1 |
| --- | --- |
| Overall Reaction Time (hours) | 6 |
| Conversion (%, molar) | 99.9 |
| ODDA Purity | 93.0 |
| Diacid Purity (%, molar) | 99.5 |
| Monoacid Impurity (%, molar) | 0.5 |

What is claimed is:

1. A method for saponifying a dibasic ester, comprising:
   introducing a dibasic ester to a reactor; and
   saponifying the dibasic ester in the reactor to form a dicarboxylate compound, wherein the saponifying comprises reacting the dibasic ester with a base in an aqueous medium;
   acidifying the dicarboxylate compound to form a dibasic acid, wherein the acidifying is carried out in an aqueous medium, whereby the dibasic acid is formed in an aqueous suspension; and
   contacting the aqueous suspension with an organic solvent to form a system having an aqueous phase and an organic phase;
   wherein the dibasic ester is a compound of formula (I):

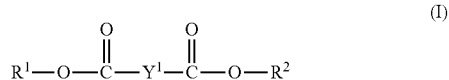

wherein:
   $Y^1$ is $-(CH_2)_{16}-$; and
   $R^1$ and $R^2$ are independently $C_{1-8}$ alkyl.

2. The method of claim 1, wherein $R^1$ and $R^2$ are independently methyl, ethyl, propyl, isopropyl, butyl, isobutyl, sec-butyl, tert-butyl, pentyl, tert-pentyl, neopentyl, hexyl, or 2-ethylhexyl.

3. The method of claim 2, wherein $R^1$ and $R^2$ are methyl.

4. The method of claim 1, wherein the base is selected from the group consisting of: an alkali metal hydroxide, an alkaline earth metal hydroxide, an alkali metal $C_{1-4}$ alkoxide, an alkaline earth metal $C_{1-4}$ alkoxide, and combinations thereof.

5. The method of claim 4, wherein the base is sodium hydroxide, potassium hydroxide, or combinations thereof.

6. The method of claim 1, wherein the dicarboxylate compound is a compound of formula (II):

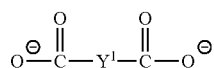

(II)

wherein $Y^1$ is as defined in claim 1.

7. The method of claim 1, wherein the dibasic acid is a compound of formula (III):

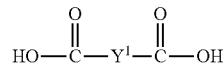

(III)

wherein $Y^1$ is as defined in claim 1.

8. The method of claim 7, wherein the acidifying comprises reacting the dicarboxylate compound with an acid.

9. The method of claim 1, wherein the organic solvent comprises toluene, ortho-xylene, meta-xylene, para-xylene, acetone, dimethylformamide, tetrahydrofuran, methylene dichloride, dimethyl sulfoxide, or any mixture thereof.

10. The method of claim 9, wherein the organic solvent comprises toluene, ortho-xylene, meta-xylene, para-xylene, or any mixture thereof.

11. The method of claim 10, wherein the organic solvent comprises toluene.

* * * * *